US012590942B2

(12) United States Patent
Strapoc et al.

(10) Patent No.: US 12,590,942 B2
(45) Date of Patent: Mar. 31, 2026

(54) MUD LOGGING OF NATURAL HYDROGEN

(71) Applicant: Schlumberger Technology Corporation, Sugar Land, TX (US)

(72) Inventors: Dariusz Strapoc, Le Plessis-Robinson (FR); Nicholas Ivars Abolins, Paris (FR); Mahdi Ammar, Clamart (FR); Aleksandar Gligorijevic, Belgrade (RS); Javier Suarez, Oklahoma City, OK (US); Harry Fowlow, Oklahoma City, OK (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/729,263

(22) PCT Filed: Mar. 28, 2023

(86) PCT No.: PCT/US2023/016484
§ 371 (c)(1),
(2) Date: Jul. 16, 2024

(87) PCT Pub. No.: WO2023/192219
PCT Pub. Date: Oct. 5, 2023

(65) Prior Publication Data
US 2025/0116648 A1      Apr. 10, 2025

Related U.S. Application Data

(60) Provisional application No. 63/481,189, filed on Jan. 24, 2023.

(30) Foreign Application Priority Data

Mar. 28, 2022   (EP) ..................................... 22305389
Apr. 26, 2022   (EP) ..................................... 22305620

(51) Int. Cl.
$G01N$ 33/28        (2006.01)
$E21B$ 21/06        (2006.01)
(Continued)

(52) U.S. Cl.
CPC ....... *$G01N$ 33/2841* (2013.01); *$E21B$ 21/067* (2013.01); *$E21B$ 49/087* (2013.01); *$G01N$ 33/2823* (2013.01); *$H01J$ 49/0009* (2013.01)

(58) Field of Classification Search
CPC ............................ E21B 49/005; E21B 21/067
See application file for complete search history.

(56) References Cited

U.S. PATENT DOCUMENTS 6,230,822 B1    5/2001   Sullivan
6,443,001 B1    9/2002   Duriez et al.
(Continued)

FOREIGN PATENT DOCUMENTS

EP        2444802 A1      4/2012
EP        2824455 A1      1/2015
(Continued)

OTHER PUBLICATIONS

Whitcar, M.J., 1990, A geochemical perspective of natural gas and atmospheric methane, Organic Chemistry, v. 16, 531-547, 17 pages.
(Continued)

*Primary Examiner* — Yanick A Akaragwe
(74) *Attorney, Agent, or Firm* — Dayo Aladeniyi

(57) ABSTRACT

A method for estimating a quantity of natural hydrogen in a subterranean formation includes degassing drilling fluid obtained from a wellbore to obtain a gas sample including a quantity of hydrogen gas, measuring a concentration of hydrogen in the gas sample, and applying a correction to the measured concentration of hydrogen to estimate the quantity of natural hydrogen in the subterranean formation.

19 Claims, 7 Drawing Sheets

(51) Int. Cl.
*E21B 49/08* (2006.01)
*H01J 49/00* (2006.01)

(56) References Cited

U.S. PATENT DOCUMENTS

| | | | |
|---|---|---|---|
| 7,392,138 B2 | 6/2008 | Frechin et al. | |
| 11,513,110 B2 | 11/2022 | Rowe | |
| 2007/0062272 A1 | 3/2007 | Frechin | |
| 2010/0153955 A1 | 6/2010 | Sirota | |
| 2010/0264315 A1 | 10/2010 | Okada | |
| 2011/0303463 A1 | 12/2011 | Lessi | |
| 2014/0231142 A1 | 8/2014 | Poitzsch | |
| 2014/0249053 A1 | 9/2014 | Robinson | |
| 2015/0322720 A1 | 11/2015 | Pelletier | |
| 2016/0003793 A1* | 1/2016 | Rowe | E21B 49/08 |
| | | | 702/11 |
| 2016/0273330 A1 | 9/2016 | Dashevsky | |
| 2016/0290131 A1* | 10/2016 | Mitchell | E21B 49/005 |
| 2017/0074094 A1 | 3/2017 | Rowe | |
| 2017/0107814 A1 | 4/2017 | Dinariev | |
| 2020/0056478 A1 | 2/2020 | Lima | |
| 2021/0285927 A1 | 9/2021 | Baecker | |
| 2022/0034862 A1 | 2/2022 | Fayez | |
| 2022/0065105 A1 | 3/2022 | Rowe | |
| 2022/0091090 A1* | 3/2022 | Baecker | G01N 33/2823 |
| 2023/0099562 A1 | 3/2023 | Alarawi | |
| 2023/0184645 A1 | 6/2023 | Smith | |
| 2024/0287898 A1 | 8/2024 | Strapoc | |

FOREIGN PATENT DOCUMENTS

| | | | |
|---|---|---|---|
| WO | 2010042383 A2 | 4/2010 | |
| WO | 2020205460 A1 | 10/2020 | |
| WO | 2022047444 A1 | 3/2022 | |
| WO | 2023278327 A1 | 1/2023 | |
| WO | 2023102528 A1 | 6/2023 | |

OTHER PUBLICATIONS

Strapoc et al., Artificial alkenes and alkanes generated during drilling: Evidence and impact on petroleum exploration. 2017, IMOG, Florence, Italy; abstract, 2 pages.

Strapoc et al., Deep biogenic methane and drilling-associated gas artifacts: impact and consequences on characterization of petroleum fluids. AAPG Bulletin v 104, Apr. 2020, pp. 887-912.

Coplen et al., New Guidelines for 13C Measurements: Analytical Chemistry, v. 78, Apr. 1, 2006, pp. 2439-2441.

Douglas et al., Methane clumped isotopes: Progress and potential for a new isotopic tracer: Organic Geochemistry, v. 113, 2017, p. 262-282.

Faber et al., Gaseous hydrocarbons of unknown origin found while drilling: Organic Geochemistry, v. 13, 1988, p. 875-879.

Herbinet et al., Thermal decomposition of n-dodecane: Experiments and kinetic modeling: Journal of Analytical and Applied Pyrolysis, v. 78, 2007, p. 419-429.

Johns et al., Combined steam reforming of methane and Fischer-Tropsch synthesis for the formation of hydrocarbons: A proof of concept study: Catalysis Letters, v. 90, 2003, p. 187-194.

Kennedy et al., Frictional melting of sedimentary rock during high-speed diamond drilling: an analytical SEM and TEM investigation: Tectonophysics, v. 204, 1992, p. 323-337.

Prinzhofer et al., New geochemical characterization of natural gas and its use in oil and gas evaluation, in M.R. Mello, and B.J. Katz, eds., Petroleum Systems of South Atlantic Margins: AAPG Memoir, v. 73, p. 107-119.

Ringer et al., Real-time motor and turbine performance monitoring and optimization: IADC/SPE Drilling Conference and Exhibition, San Diego, CA, USA, Mar. 6-8, 2012, IADC/SPE 151451, 7 pages.

Wenger et al., Drill-bit metamorphism: Recognition and impact on show evaluation: Society of Petroleum Engineers, 125218-MS, Paper presented at the SPE Annual Technical Conference and Exhibition, New Orleans, Louisiana, Oct. 2009, 9 pages.

Xing et al., Kinetics and Product Distributions for Thermal Cracking of a Kerosene-Based Aviation Fuel: Energy Fuels, v. 23, 2009, p. 4021-4024.

Qubaisi et al., Using Drill Bit Metamorphism to Aid in Formation Evaluation of Tight Gas Reservoirs, IPTC-20353-MS, International Petroleum Technology Conference, Jan. 13, 2020, pp. 1-9 pp. 4-5.

Key role of regearing mud gas logging for natural hydrogen exploration, Abstract Id: 1315 for SPWLA 63rd Annual Logging Symposium, Nov. 7, 2021, 3 pages.

Han et al., On-line multi-component analysis of gases for mud logging industry using data driven Raman spectroscopy. Fuel, 207, 2017, 146-153.

Strapoc et al., Controlled drill bit metamorphism (DBM) using indoor rig floor experiments. Virtual poster presented at IMOG, Sep. 12-17, 2021, Montpelier, France, 1 page.

Wang et al., A review of cavity-enhanced Raman spectroscopy as a gas sensing method. Applied Spectroscopy Reviews, 55(5), 393-417.

* cited by examiner

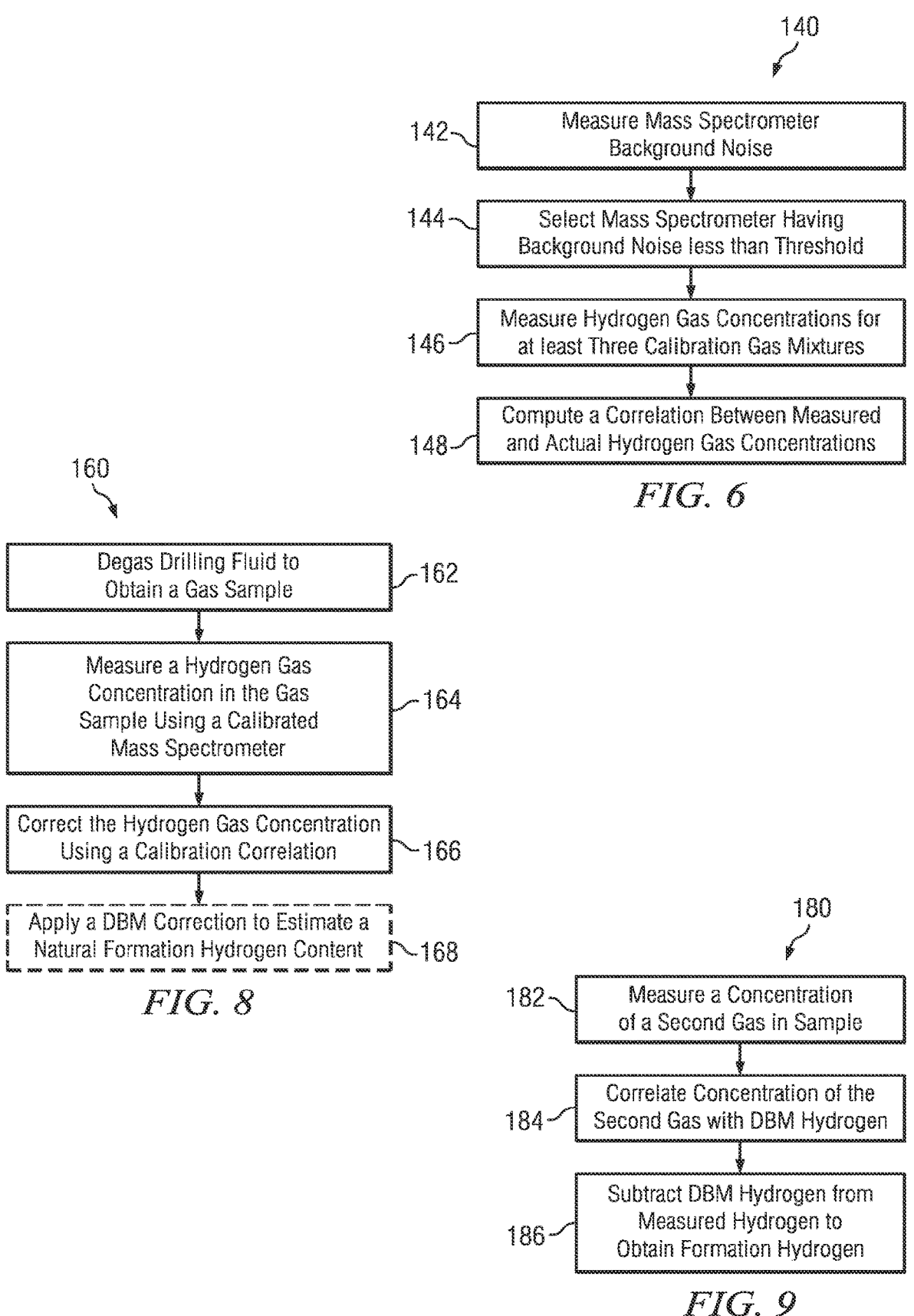

140

142 — Measure Mass Spectrometer Background Noise

144 — Select Mass Spectrometer Having Background Noise less than Threshold

146 — Measure Hydrogen Gas Concentrations for at least Three Calibration Gas Mixtures 148 — Compute a Correlation Between Measured and Actual Hydrogen Gas Concentrations

162 — Degas Drilling Fluid to Obtain a Gas Sample

164 — Measure a Hydrogen Gas Concentration in the Gas Sample Using a Calibrated Mass Spectrometer 166 — Correct the Hydrogen Gas Concentration Using a Calibration Correlation 168 — Apply a DBM Correction to Estimate a Natural Formation Hydrogen Content

182 — Measure a Concentration of a Second Gas in Sample

184 — Correlate Concentration of the Second Gas with DBM Hydrogen

186 — Subtract DBM Hydrogen from Measured Hydrogen to Obtain Formation Hydrogen

*FIG. 9*

MUD LOGGING OF NATURAL HYDROGEN

CROSS REFERENCE TO RELATED APPLICATIONS

This application is a National Stage Entry of International Application No. PCT/US2023/016484, filed Mar. 28, 2023, which claims the benefit of European Patent Application No. 22305389.3, which was filed on Mar. 28, 2022, European Patent Application No. 22305620.1, which was filed on Apr. 26, 2022, and U.S. Provisional Application No. 63/481,189, which was filed on Jan. 24, 2023. Each of the patent applications identified above is incorporated herein by reference in its entirety.

BACKGROUND

The global demand for hydrogen continues to grow. At the time of this disclosure the majority of global hydrogen use is for refining hydrocarbons and for the production of industrial fertilizers. In recent years there has been a significant increase in the development and use of renewable energy sources with hydrogen being expected by many to have an important role as a clean energy carrier and currency. As such, some forecasters are projecting a five to ten fold increase in hydrogen demand over the next 20 years.

Over 90 percent of commercial hydrogen is currently generated by burning hydrocarbons (e.g., natural gas) in the presence of steam. To meet the projected demand increase there is an interest in developing new hydrogen sources. For example, methods for extracting naturally occurring hydrogen from subterranean formations are being explored (e.g., via drilling in a manner similar to that used to obtain hydrocarbons). There is a need in the industry for methods and systems for sensing and quantifying naturally occurring hydrogen in subterranean formations, for example, during drilling operations.

BRIEF DESCRIPTION OF THE DRAWINGS

For a more complete understanding of the disclosed subject matter, and advantages thereof, reference is now made to the following descriptions taken in conjunction with the accompanying drawings, in which:

FIG. 6 depicts a flow chart of one example method embodiment for calibrating a mass spectrometer for measuring a hydrogen gas concentration.

FIG. 8 depicts a flow chart of another example method for estimating a quantity of naturally occurring hydrogen in a subterranean formation.

FIG. 9 depicts a flow chart of one example method for applying a DBM correction in the flow chart depicted on FIG. 8.

DETAILED DESCRIPTION

The disclosed embodiments may provide an improved methodology for quantifying natural hydrogen in a subterranean formation, for example, in which drill bit metamorphism hydrogen is removed from the measurement. In one embodiment a method for estimating a quantity of natural hydrogen in a subterranean formation includes degassing drilling fluid obtained from a wellbore to obtain a gas sample including a quantity of hydrogen gas, measuring a concentration of hydrogen in the gas sample, and applying a correction to the measured concentration of hydrogen to estimate the quantity of natural hydrogen in the subterranean formation. In example embodiments the concentration of hydrogen gas may be measured using a mass spectrometer calibrated for making hydrogen measurements.

Figure 1:
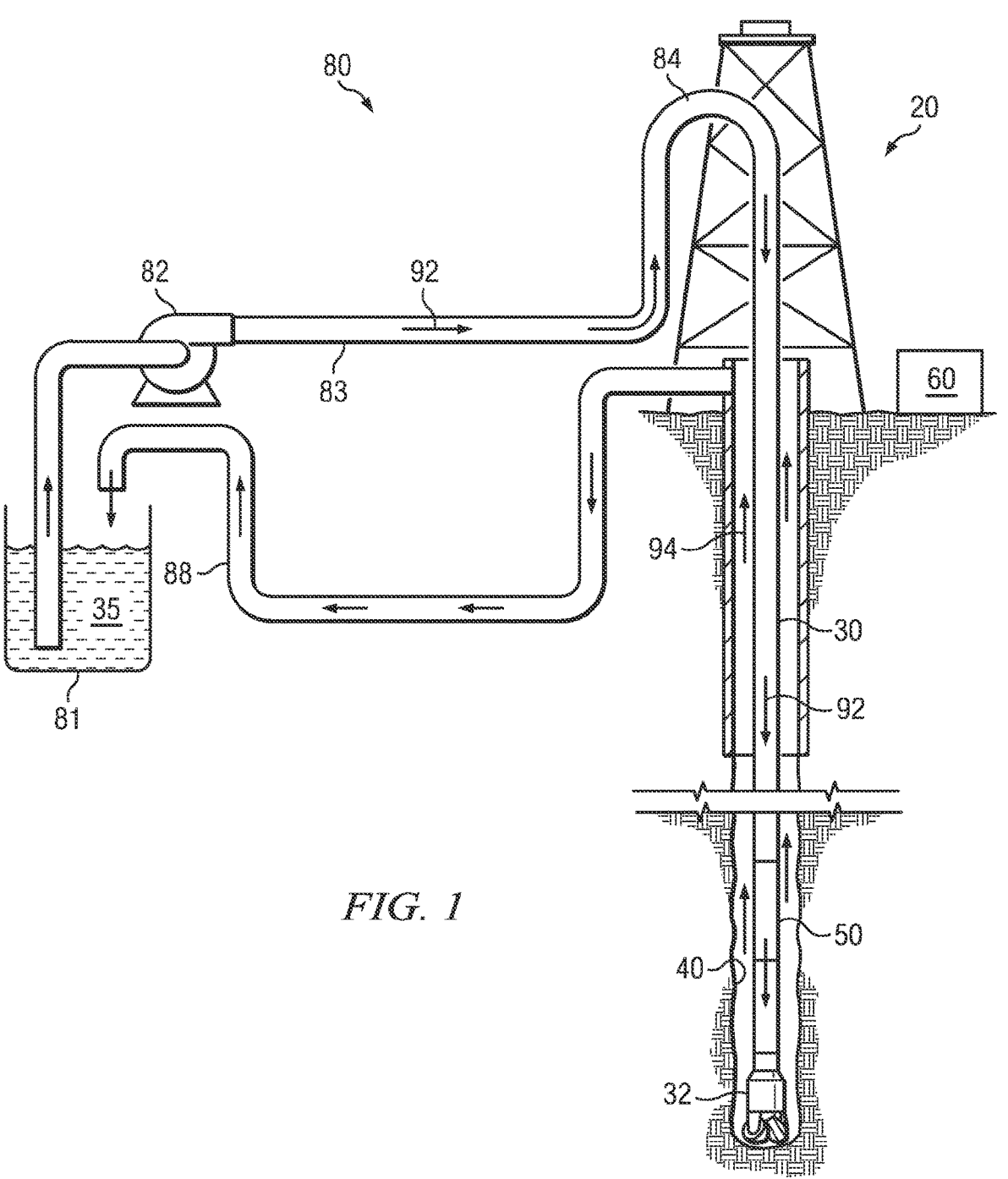
FIG. 1 depicts an example drilling rig including a surface system for sensing and quantifying naturally occurring hydrogen gas.

FIG. 1 depicts an example drilling rig 20 including a system for sensing and quantifying naturally occurring hydrogen gas. The drilling rig 10 may be positioned over a subterranean formation (not shown). The rig may include, for example, a derrick and a hoisting apparatus (also not shown) for raising and lowering a drill string 30, which, as shown, extends into wellbore 40 and includes, for example, a drill bit 32 and one or more downhole measurement tools 50 (e.g., a logging while drilling tool or a measurement while drilling tool). Suitable drilling systems, for example, including drilling, steering, logging, and other downhole tools are well known in the art.

Drilling rig 20 further includes a surface system 80 for controlling the flow of drilling fluid used on the rig (e.g., used in drilling the wellbore 40). In the example rig depicted, drilling fluid 35 is pumped downhole (as depicted at 92) via a conventional mud pump 82. The drilling fluid 35 may be pumped, for example, through a standpipe 83 and mud hose 84 in route to the drill string 30. The drilling fluid typically emerges from the drill string 30 at or near the drill bit 32 and creates an upward flow 94 of mud through the wellbore annulus (the annular space between the drill string and the wellbore wall). The drilling fluid then flows through a return conduit 88 to a mud pit 81. It will be appreciated that the terms drilling fluid and mud are used synonymously herein.

The disclosed embodiment may include methods and systems for sensing and quantifying naturally occurring hydrogen in a drilling fluid. By naturally occurring, it is meant that the hydrogen originates in a subterranean formation. The naturally occurring hydrogen migrates from the formation (e.g., via fractures and interstitial space in the rock) to the wellbore 40 and is transported to the surface via the drilling fluid (in the upwardly flowing fluid 94). The naturally occurring hydrogen is sampled in the surface system, for example, via one or more drilling fluid degassers 97, 98 (FIG. 2) deployed, for example, in the return conduit

88 or the mud pit 91 and/or a head space gas probe 99 (FIG. 2) deployed, for example, in the return conduit 88.

With further reference to FIG. 1, drilling rig 20 may further include a hydrogen testing facility 60 (e.g., a laboratory trailer including one or more instruments suitable for detecting hydrogen in a gas stream). The instruments may include, for example, a calibrated mass spectrometer, such as a quadrupole mass spectrometer, a gas chromatograph, a thermal conductivity detector, an infrared or near-infrared spectrometer, and/or a Raman spectrometer among others. One example quadrupole mass spectrometer is the portable DQ1000 wellsite mass spectrometer gas analyzer available from SLB. The instruments may also be portable (and are not necessarily confined to a lab or to the wellsite).

Figures 2, 3, 4:
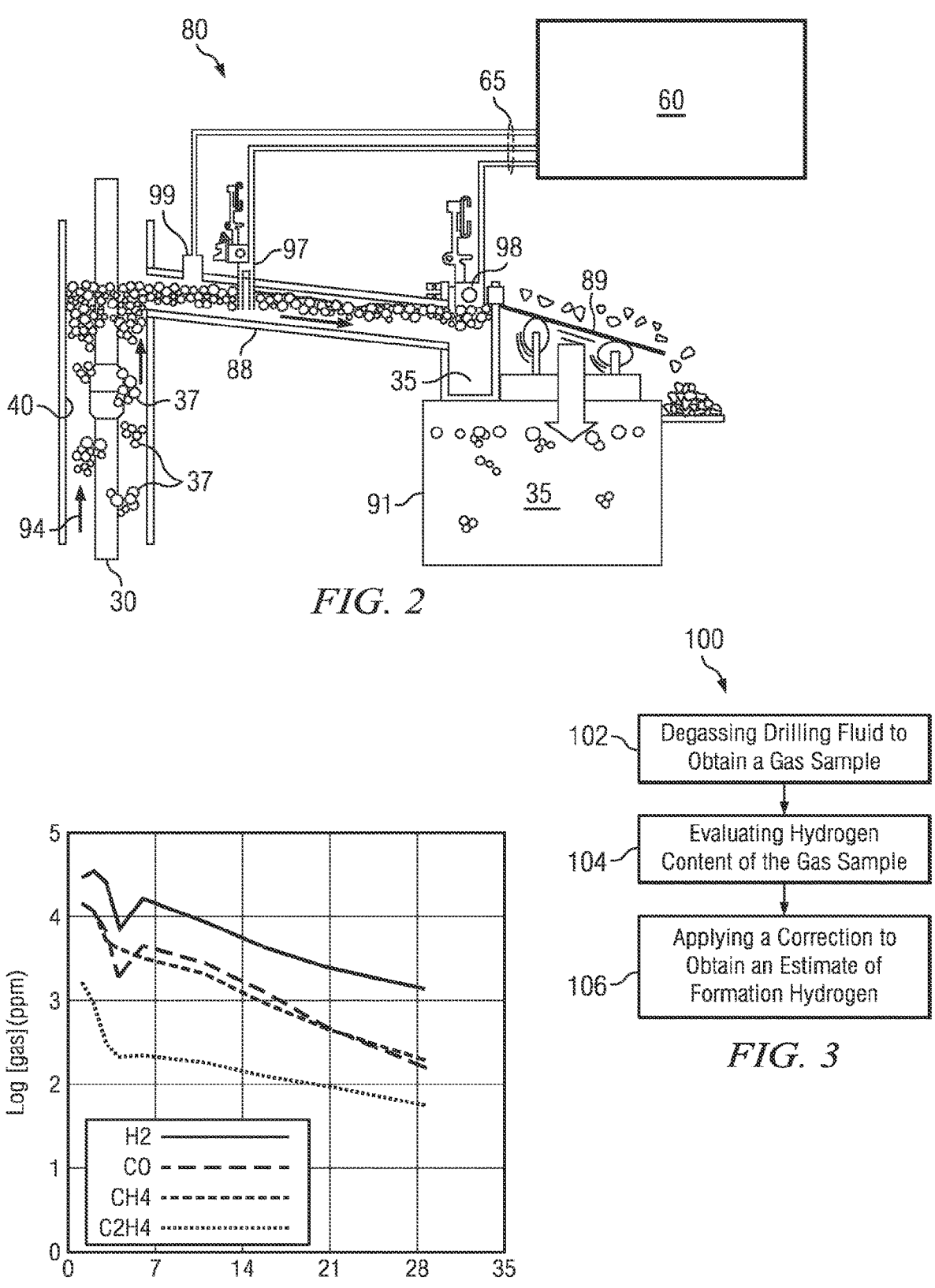
FIG. 2 depicts another embodiment of a surface system for sensing and quantifying naturally occurring hydrogen gas.
FIG. 3 depicts a flow chart of one example method embodiment for estimating a naturally occurring hydrogen content of a subterranean formation.
FIG. 4 depicts a log plot of measured gas concentration (in units of ppm by weight) versus time while recirculating a drilling fluid in one example logging operation.

FIG. 2 depicts another embodiment of surface system 80 including a return conduit 88 configured to carry drilling fluid 35 (sometimes including bubbles 37) from wellbore 40 to mud pit 91. The example system 80 includes a degasser 98 deployed, for example, adjacent to the mud pit 91 and shale shaker 89 (at the outlet of return conduit 88) and/or a degasser 97 deployed along the conduit 88 and including a probe configured to sample drilling fluid prior to its exposure to air as depicted. The system 80 may further include a gas probe 99 configured to sample gas in the conduit 88 or wellbore head space. The degasser(s) 97, 98 and/or gas probe 99 may be piped to laboratory 60 (as depicted at 65), for example, to automatically transport the sampled gases to the lab for testing. System 80 may include substantially any suitable degasser 97, 98, for example, including a vacuum degasser, a centrifugal degasser, and an impeller degasser. The degasser 97, 98 may further be configured to heat the drilling fluid 35 to promote full degassing of the fluid. The disclosed embodiments are not limited in regard to the type of degasser employed. Moreover, while not depicted, the system 80 may include one or more pumps (e.g., suction or pressure boosting pumps) configured to pump sampled gas from the degasser(s) 97, 98 and/or the probe 99 to the laboratory 60. The disclosed embodiments are, of course, not limited in regards to any pumping or gas transport piping.

FIG. 3 depicts a flow chart of one example method 100 for estimating a quantity of naturally occurring hydrogen in a subterranean formation. The method includes degassing drilling fluid to obtain a gas sample at 102, evaluating a quantity of hydrogen gas (e.g., a concentration of hydrogen gas) in the gas sample at 104, and applying a correction to the quantity of hydrogen gas measured at 104 to obtain an estimate of natural formation hydrogen at 106.

As noted above with respect to FIG. 2, substantially any suitable degasser may be employed to obtain the gas sample at 102. The degasser may be deployed along a return conduit that transports drilling fluid from the well to the mud pit. In other embodiments, the degasser may be configured to degas drilling fluid located near or even in the mud pit.

One expected challenge in obtaining a gas sample having a representative quantity (e.g., concentration) of hydrogen gas is the low solubility of hydrogen (e.g., about 1-2 ppm by weight in water). Therefore, it may be advantageous in certain embodiments to sample drilling fluid prior to its exposure to air by deploying a degasser probe directly in the fluid in the return conduit (e.g., as depicted on FIG. 2 at 97) or via using a drilling fluid flow line bypass (not depicted). Such configurations may be advantageous, for example, when water-based drilling fluid is employed since the solubility of hydrogen in water-based fluids is believed to be less than that of oil-based fluids. Notwithstanding, the disclosed embodiments are not limited in these regards.

Obtaining a gas sample at 102 may further include obtaining a gas sample from head space at the top of the wellbore (e.g., just below the nipple) or along the return conduit (e.g., as depicted on FIG. 2). Those of ordinary skill will readily appreciate that drilling fluid often begins degassing as it returns to the surface (and atmospheric pressure). The head space may sometimes include hydrogen gas (along with other gases) owing to the natural degassing process of the fluid as it returns to atmospheric pressure.

Various degasser configurations have been tested. In one example test, drilling fluid was sampled directly from a mud flowline bypass to a degasser (with no exposure of the fluid to air prior to the degassing chamber). The sampled gas from the bypass showed high and reliable readings of hydrogen. Moreover, after drilling was stopped and the drill bit was lifted off the bottom of the well, the fluid was recycled through an open mud pit and back into the well loop. Sampling and evaluation of the gas continued for 30 minutes during recirculation.

FIG. 4 depicts a log plot of the measured gas concentration (in units of ppm by weight) versus time while recirculating the drilling fluid through the well. Concentrations of hydrogen, ethylene, carbon monoxide, and methane gas were measured. The gas concentrations were observed to decrease with time as the fluid naturally degassed. Degassing rates may be estimated from the slope of the respective curves with time. Note that the rate of hydrogen degassing in the circulating fluid was similar to that of carbon monoxide and ethylene with the gas concentrations decreasing by about an order of magnitude in about 20 minutes. This surprising result implies that despite its low solubility, hydrogen gas tends to remain in the drill fluid and only degasses slowly (even during fluid recirculation).

While the disclosed embodiments are not limited to the use of any particular type of degasser, it will be understood that certain degasser configurations may be advantageous in various operations. For example, in operations in which hydrogen degassing is relatively slow (as with the surprising data shown in FIG. 4), the use of more aggressive degassing techniques may be advantageous. Such techniques may include an impeller or sonication to mechanically agitate the drilling fluid, vacuum to draw gas out of the fluid, heating the fluid to promote degassing, and/or degassing the fluid as it recirculates in a loop at the surface to provide more time for degassing. Particularly aggressive degassing techniques may include heating and/or the use of a recirculation loop at the surface. In operations in which hydrogen degassing occurs more readily such aggressive degassing techniques may not be necessary, and it may be advantageous to sample head space gases as described above with respect to FIG. 2.

In another example test, gas was sampled from both an inline gas trap (probe) that sampled the head space in the return conduit (e.g., as depicted at 99 in FIG. 2) and a degasser located at the outlet of the conduit adjacent to the mud pit (e.g., as depicted at 98 on FIG. 2). The collected gases were analyzed using corresponding DQ1000 mass spectrometers.

Figure 5:
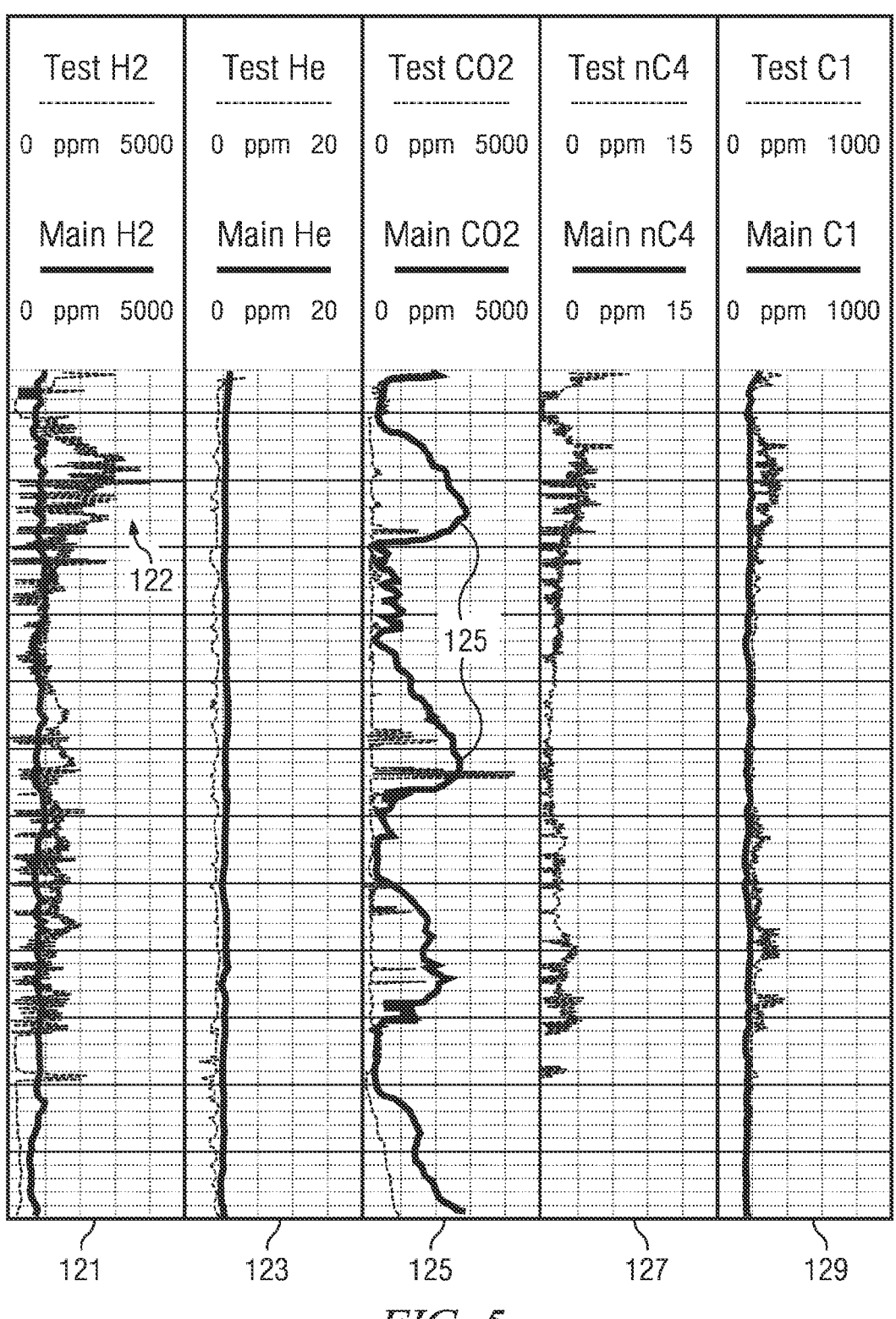
FIG. 5 depicts a drilling log including head space and degasser gas concentrations versus time.

FIG. 5 depicts a log of gas concentrations versus time with the head space gases referred to as 'Test' and the degasser gases referred to as 'Main'. The log depicts hydrogen concentrations at 121, helium concentrations at 123, carbon dioxide concentrations at 125, butane (C4) concentrations at 127, and methane (C1) concentrations at 129. The concentrations of each gas (hydrogen, helium, carbon dioxide, butane, and methane) are indicated on the horizontal axes (e.g., from 0 to 5000 ppm for hydrogen and carbon dioxide). It was expected that higher hydrogen concentrations would be observed in the head space gases, owing to the presumed low solubility of hydrogen in the drilling fluid. However, counterintuitively it was observed that the hydrogen levels remained below 1000 ppm in the head space gases while much larger hydrogen gas levels were observed in the degasser gases (e.g., up to 5000 ppm as depicted at 122).

The behavior of hydrogen was significantly different than that of carbon dioxide which had significantly higher concentrations in the head space (e.g., by about a factor of 3 in the peaks observed at 126). These results support the surprising affinity of hydrogen to remain in the drilling fluid (or to degas slowly from the flowing mud) despite its volatility and presumed low solubility. In certain operations (using particular drilling fluids), the liberation of hydrogen gas from flowing drilling fluid may be low enough to permit the use of a conventional degasser at the outlet of the return conduit. In such embodiments, the liberation of hydrogen gas may be slow enough that use of a heated degasser and/or a recirculating degasser may be advantageous to ensure that most/all of the hydrogen gas is degassed from the fluid.

With reference again to FIG. 3, the quantity of hydrogen in the gas sample may be evaluated at 104 using substantially any suitable technique or sensor, for example, including mass spectrometry, gas chromatography, and/or solid state hydrogen gas sensors. In certain embodiments the gas evaluation in 104 may make use of mass spectrometry techniques that are commonly employed at a rig site to evaluate other wellbore gases such as methane, butane, and carbon dioxide. Although not always required, it may be advantageous to calibrate a rig site mass spectrometer to detect and quantify hydrogen gas in the degassed gas stream. A suitable calibration procedure may include evaluating a plurality of gas samples having known hydrogen concentrations and developing a correlation between the mass spectrometry measurements and the known hydrogen concentrations in the samples.

In example embodiments, the mass spectrometer may include a DQ1000 mass spectrometer (a portable quadrupole mass analyser commonly used in well drilling operations). Calibration of the DQ1000 may make use of multi-point calibration techniques using a plurality of gas mixtures having varying hydrogen gas concentration. The calibration may advantageously cover a wide range of hydrogen gas concentrations, for example, from parts per million (ppm) levels to nearly 100 percent. The use of a mass spectrometer, such as a DQ1000, may advantageously provide a short analysis cycle time, thereby providing for high frequency data in time and depth (e.g., as drilling progresses) that enables the generation of a hydrogen gas log depicting naturally occurring hydrogen levels versus measured depth of the wellbore.

While the disclosed embodiments are not limited in this regard, common occurrences of hydrogen (and helium in certain formations) are expected in relatively small scale (size) geological features, such as near fractures (e.g., in crystalline rocks) or faults, which may serve as conduits from deeper source rocks or lower crust/upper mantle vents. Examples include fractured granite basement or uplifted and fractured shallow mafic rocks, which when exposed to water may undergo hydrogen generating reactions. The disclosed embodiments may advantageously enable a log of naturally occurring hydrogen to be generated which may in turn enable a drilling operator to locate subterranean hydrogen sources (or conduits).

Turning now to FIG. 6, a flow chart of an example method 140 for calibrating a mass spectrometer, such as a quadrupole mass spectrometer, for making quantitative measurements of hydrogen gas is depicted. A background noise level is determined for the mass spectrometer at 142. The background noise level may be determined, for example, by making a hydrogen measurement while flushing the spectrometer with air (e.g., for at least two hours prior to making the measurement). Mass spectrometers having a background noise level less than a predetermined threshold (e.g., less than 1000 ppm or less than 500 ppm) may be selected at 144 for further calibration. At least three calibration gas mixtures having three distinct hydrogen gas concentrations may be evaluated using a selected mass spectrometer at 146. The calibration gas mixtures may have substantially any suitable hydrogen gas concentrations provided that they span a hydrogen concentration of interest (e.g., spanning at least two orders of magnitude in concentration). In one example embodiment, three calibration gas mixtures having hydrogen gas concentrations of 0.1, 1.0, and 10 percent (1000 ppm, 10000 ppm and 100000 ppm) hydrogen gas may be evaluated. The remainder of the calibration gas mixture may include, for example, nitrogen. The hydrogen concentration measurements made at 146 may be evaluated at 148 to compute a correlation or a best fit between the measured hydrogen concentrations and the actual (or known) hydrogen concentrations. In certain advantageous embodiments, the correlation may be a linear-log fit or an exponential fit.

With continued reference to FIG. 6, the background noise and the hydrogen gas concentration of the calibration samples may be evaluated at 142 and 146 via evaluating a mass over charge ratio equal to two (i.e., m/z=2, where m represents mass and z represents charge). A mass over charge ratio of two corresponds to hydrogen species having a diatomic molecular structure ($H_2$). In example calibrations, it has been found that each mass spectrometer has an appreciable hydrogen background noise (or offset), generally in the range from about 300 to about 3000 ppm. While not wishing to be bound by theory, it is believed that this background noise is caused by the so called "m/z=1 blast effect". It was observed that the background noise varies from mass spectrometer to mass spectrometer and it is believed that it may drift with the age of the mass spectrometer. As such only mass spectrometers having a background noise less than a threshold value (e.g., 1000 ppm or 500 ppm) are selected for further calibration at 104. Table 1 lists background hydrogen levels for five example mass spectrometers.

TABLE 1

| Mass Spectrometer | Background $H_2$ (ppm) |
|---|---|
| A | 2565 |
| B | 999 |
| C | 366 |
| D | 416 |
| E | 346 |

With continued reference to FIG. 6, it was further found that the mass spectrometers overestimated (exaggerated or amplified) the hydrogen concentration in the calibration gas mixtures. The pattern of hydrogen amplification was complex with the amplification (also referred to herein as a bias) decreasing with increasing hydrogen concentration in the calibration samples. Table 2 lists measured hydrogen gas concentrations obtained using the same five example mass spectrometers listed in Table 1. Three calibration gas mixtures were measured, having actual hydrogen gas concentrations of 1000 ppm (0.1%), 10000 ppm (1%), and 100000 ppm (10%) in this example. Note that for each mass spectrometer the measured hydrogen concentration was at least a factor of three greater than the actual hydrogen concentration. Moreover, the bias (amplification) was found to be weakly associated with the background noise level, with mass spectrometers that had a higher background noise level generally also having a higher amplification. Furthermore, the bias was also found to decrease with increasing hydrogen content in the calibration sample.

TABLE 2

| Mass Spectrometer | Sample 1 (0.1% $H_2$) | | Sample 2 (1.0% $H_2$) | | Sample 3 (10% $H_2$) | |
|---|---|---|---|---|---|---|
| | Measured | Bias | Measured | Bias | Measured | Bias |
| A | 3.17 | 31.7 | 27.0 | 27.0 | 112 | 11.2 |
| B | 1.36 | 13.6 | 11.8 | 11.8 | 85.4 | 8.5 |
| C | 0.76 | 7.6 | 7.1 | 7.1 | 53.4 | 5.3 |
| D | 1.37 | 13.7 | 12.3 | 12.3 | 85.7 | 8.6 |
| E | 0.34 | 3.4 | 2.9 | 2.9 | 24.9 | 2.5 |

Figure 7:
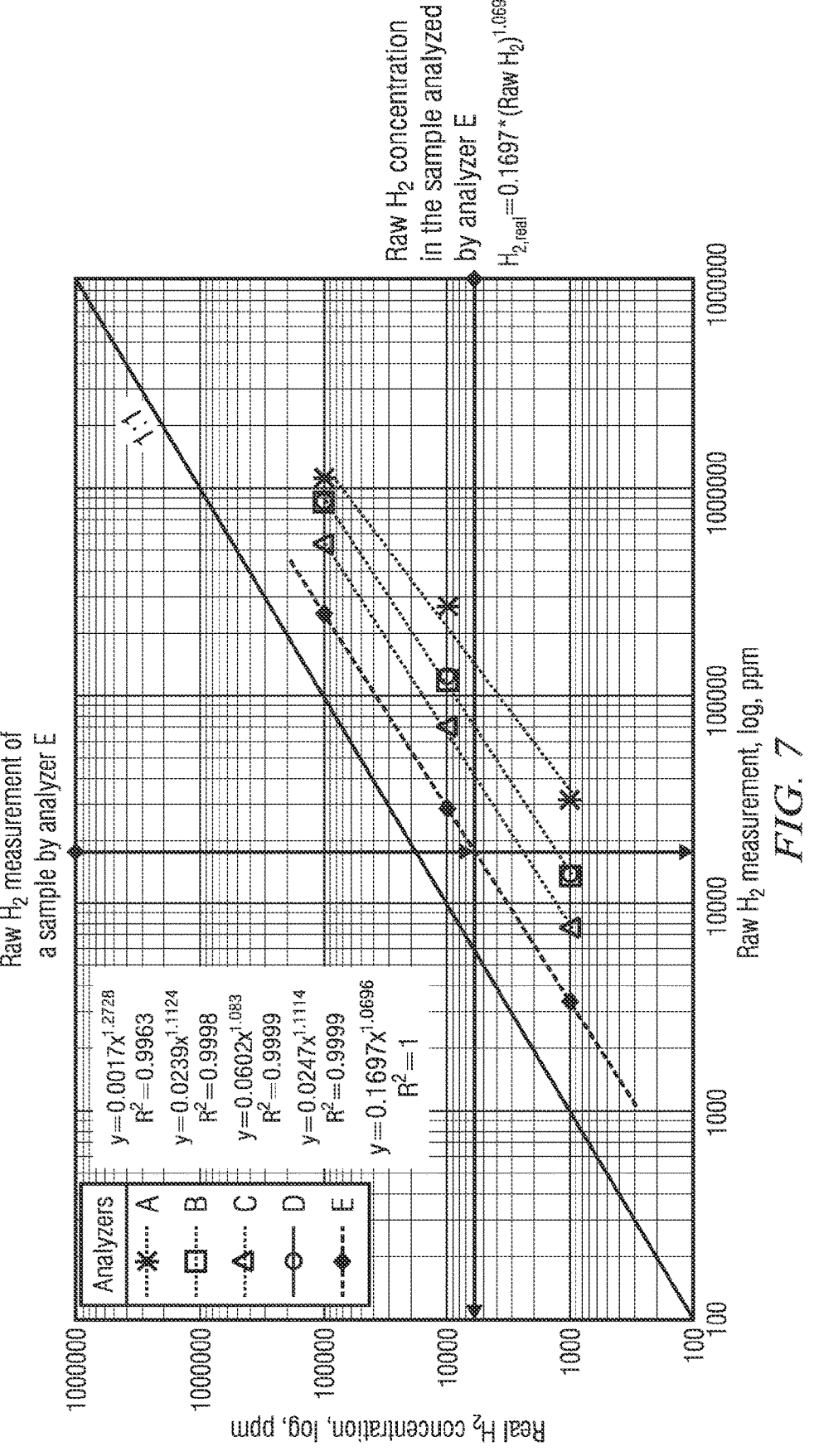
FIG. 7 depicts a log plot of measured gas concentration (in units of ppm by weight) versus time while recirculating a drilling fluid in one example logging operation.

FIG. 7 depicts a plot of the actual hydrogen concentration in the three calibration samples (0.1%, 1%, and 10%) versus the mass spectrometer measurements obtained at 106 using mass spectrometers A, B, C, D, and E. FIG. 7 also depicts a best fit (a mathematical correlation) that equates the actual hydrogen gas concentration and the measured hydrogen gas concentration for each of the mass spectrometers. It was observed that the correlations for the mass spectrometers having a background noise of less than 1000 ppm had $R^2$ values greater than 0.999.

FIG. 7 further depicts a hypothetical measurement for an unknown sample using mass spectrometer E. In this example, the raw hydrogen ($H_2$) concentration measurement was 18100 ppm (1.81%) indicating an actual hydrogen ($H_2$) concentration in the unknown sample of 6080 ppm (0.608%). As indicated on the plot the measured $H_2$ concentration is substituted into the correlation ($0.1697 \cdot (\mathrm{RawH_2})^{1.0696}$) to obtain the actual hydrogen concentration of the unknown sample.

It will be appreciated that owing to the amplification (the bias), the saturation of any particular mass spectrometer was reached at a hydrogen concentration of less than 100%. For example, saturation will occur at a hydrogen concentration of 20% if the bias is about equal to five. As noted above, it was also found that the bias decreased with increasing hydrogen concentration (with an $r^2 > 0.9$).

It will be appreciated that the above described calibration method may be further refined, for example, by taking into account other measurement variables, such as the temperature of the calibration gas sample (or the temperature of the laboratory environment in which the calibration measurements are made or the temperature within the mass spectrometer chassis), the moisture content of the calibration gas samples (e.g., by evaluating a mass over charge ratio of 18 in the mass spectrometer measurements, and/or a concentration of nitrogen in air (e.g., by evaluating a mass over charge ratio of 28). These other measurement variables may be further correlated with the actual hydrogen gas concentration in the calibration gas samples to obtain a multivariable calibration. The disclosed embodiments are, or course, not limited in this regard.

With still further reference to FIG. 3, applying a correction to the hydrogen gas measurement at 106 may include, for example, correcting the hydrogen measurements for drill bit metamorphism (DBM) by-products. One aspect of the disclosed embodiments was the realization that the hydrogen gas arriving within the drilling fluid flowline (e.g., in the fluid or head space), even if perfectly extracted and analyzed, might not be representative of the naturally occurring hydrogen derived from the drilled formation. It was further realized that hydrogen gas content in the drilling fluid can be artificially magnified by the drilling process.

For example, hydrogen gas may sometimes be generated at the interface between the drill bit and the formation when bit temperatures are high (particularly when using oil-based drilling fluid). In such operations alkanes in the oil-based mud (OBM) may be "cracked" when the local heating surpasses the activation energy of the alkanes thereby partially transforming the OBM alkanes to shorter chain molecules (including hydrogen gas when the temperature is sufficiently high). Such DBM tends to be related to many drilling and rock parameters, such as rock strength, abrasiveness, hardness of the cutting elements, sliding surface areas, friction areas, weight on bit, vibrations, torque, effectiveness of bit cooling which corresponds to the mud flow rate and mud and cutter/bit heat transfer rate. For example, DBM might occur more often when the drill bit rotation speed is particularly high and drilling fluid flow rates are low thereby resulting in increased drilling temperatures. Example DBM correction methods are described in more detail below.

Turning now to FIG. 8, a flow chart of an example method 160 for estimating a quantity of naturally occurring hydrogen in a subterranean formation is depicted. The method includes degassing drilling fluid to obtain a gas sample at 162 and measuring a quantity of hydrogen gas (e.g., a concentration of hydrogen gas) in the gas sample at 164 using a calibrated mass spectrometer (e.g., a DQ1000 mass spectrometer calibrated using method 140). The quantity of hydrogen gas measured at 164 is the corrected using a calibration correlation (e.g., as computed at 148 of method 140) to compute the concentration of hydrogen gas in the gas sample at 166. The concentration of hydrogen gas computed at 166 may then be optionally further processed, for example, to correct for DBM hydrogen at 168 to obtain an estimate of natural formation hydrogen.

FIG. 9 depicts a flow chart of one example method 180 for correcting the hydrogen gas measurement at 168 of method 160 (FIG. 8). The method 180 may include measuring a content of a second gas (or multiple second gases) at 182 in the gas sample obtained at 162 (FIG. 8). The second gas(es) may be measured, for example, concurrently with the hydrogen gas measurement made at 164 (e.g., using the mass spectrometer used to measure the hydrogen gas concentration). The second gas(es) may include, for example, carbon monoxide or an alkene such as ethylene, butylene, or propylene. The method 180 for correcting the hydrogen gas measurement may further include correlating the second gas measurement(s) with a model (or mathematical equation) to determine a quantity (or concentration) of DBM hydrogen in the gas sample at 184 and subtracting the DBM hydrogen from the hydrogen content measured at 164 (FIG. 8) to obtain the estimate of formation hydrogen at 186.

It has been found that the concentration of DBM hydrogen is closely related to the concentration of other gases in the gas stream, for example, including carbon monoxide, ethylene, butylene, and/or propylene. Empirical data may be used to generate correlations of DBM hydrogen to another gas concentrations (e.g., carbon monoxide). The correlation may also include other variables, for example, including a temperature measurement made at the bit, drill string rotation rate, drill string torque, weight on bit, drilling fluid flow rate, and the like. The correlation may also include the formation type (e.g., shale, sandstone, granite, etc.) as well as the type of drilling fluid (e.g., oil-base or water-base drilling fluid) and/or the composition of the drilling fluid (e.g., the composition of the base oil in the drilling fluid).

Figure 10A:
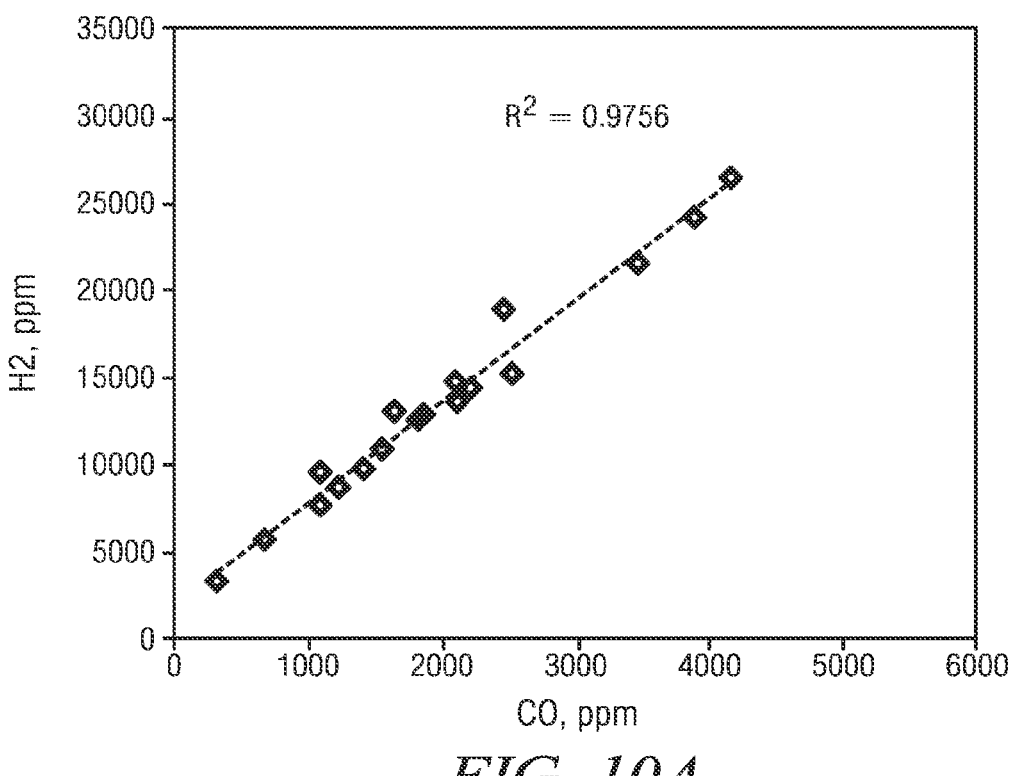
FIGS. 10A and 10B (collectively FIG. 10) depict plots of hydrogen gas concentration versus carbon monoxide gas concentration (10A) and hydrogen gas concentration versus alkene gas concentration (10B) (all in ppm) for an example drilling operation.
Figure 10B:
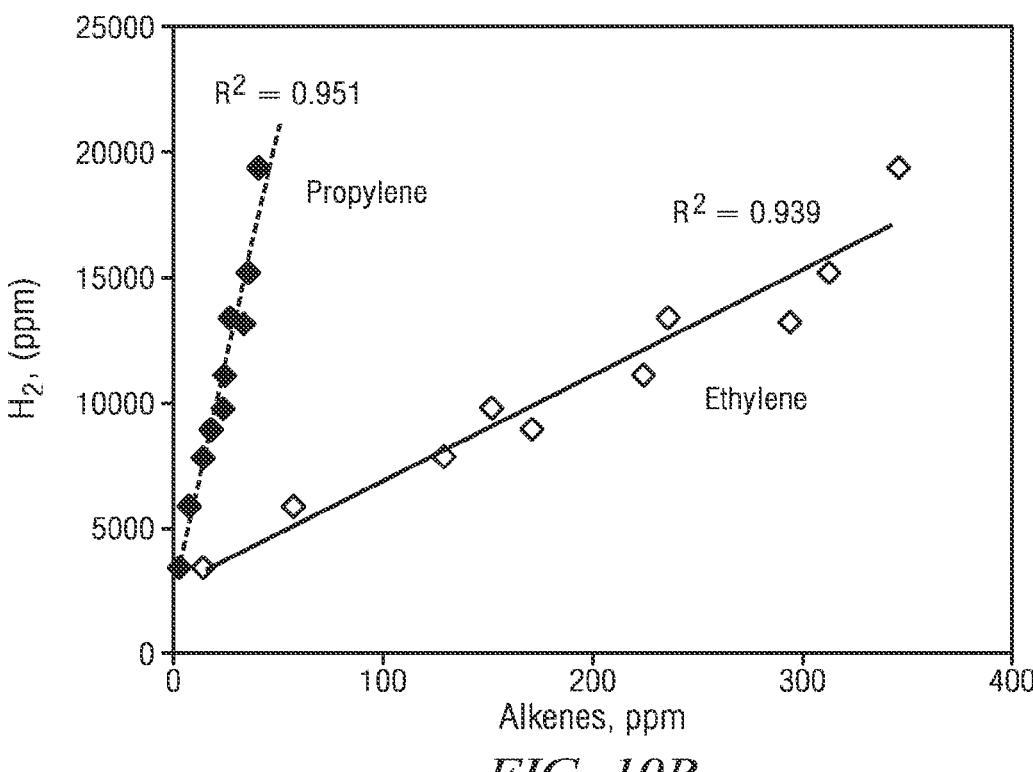

FIGS. 10A and 10B (collectively FIG. 10) depict plots of hydrogen gas concentration versus carbon monoxide gas concentration (10A) and hydrogen gas concentration versus alkene gas concentration (10B) (all in ppm) for an example drilling operation. In this example operation, the well was drilled through clean sandstone (including no indigenous hydrocarbons or hydrogen) using oil-based mud (OBM). The plots show correlations between measured hydrogen gas and carbon monoxide, ethylene, and propylene gas concentrations in which the hydrogen gas concentration increased approximately linearly with the concentrations of carbon monoxide, ethylene, and propylene. In FIG. 10A, the hydrogen gas concentration was observed to increase linearly with increasing carbon monoxide gas concentration with a slope of about 6. In FIG. 10B, the hydrogen gas concentration was observed to increase linearly with increasing ethylene and propylene gas concentrations with corresponding slopes of about 20 and about 380. In this example, the increased hydrogen, carbon monoxide, ethylene, and propylene gas levels resulted from increased heating owing to a controlled elevation of power input to the drill bit. The hydrogen was presumed to be essentially all DBM hydrogen as the formation did not include any naturally occurring hydrogen. The depicted correlations may enable DBM hydrogen levels to be obtained from carbon monoxide, ethylene, and/or propylene measurements. Determining DBM hydrogen gas levels from carbon monoxide measurements may be particularly advantageous since carbon monoxide does not generally occur in unmined, deep subsurface geological formations (having no access to atmospheric oxygen).

While FIG. 10 depicts example correlations between measured carbon monoxide, ethylene, and propylene and DBM hydrogen gas, it will be understood that the disclosed embodiments are not limited to any particular correlation (empirical or otherwise). Suitable correlations may be linear or nonlinear and may include, for example, an analytical equation that correlates a concentration of the second gas (e.g., carbon monoxide, ethylene, and/or propylene) with a concentration of DBM hydrogen. In another embodiment, the correlation may include a look-up table that correlates a concentration of the second gas (e.g., carbon monoxide) with a concentration of DBM hydrogen. The disclosed embodiments are not limited in these regards.

In certain embodiments, DBM hydrogen may be measured (or estimated) based on other drilling fluid logging measurements such as gas chromatography. For example only, DBM hydrogen values may be estimated based on measurements from a commercially available wellsite gas analyzer configured to measure continuous total gas, alkanes, and alkenes (such as PureFlex-DBM measurements available from Schlumberger). In such embodiments, the alkene measurements may be processed with a correlation (e.g., as shown in FIG. 10B) to obtain the DBM hydrogen levels as described above. As described above, disclosed embodiments may include assembling a log of naturally occurring hydrogen with measured depth of a wellbore. Such a log may further depict the measured quantity of hydrogen gas, measured quantities of other gases such as carbon monoxide, ethylene, and propylene, and the correlated DBM hydrogen gas level.

While the disclosed embodiments may advantageously make use of a calibrated mass spectrometer as described above, it will be appreciated that other techniques for measuring the hydrogen gas concentration may be employed. For example, a dedicated hydrogen gas analyser may include, for example, a laser absorption spectroscopy technique such as tunable diode laser absorption spectroscopy or cavity ring-down spectroscopy. These absorption-based techniques tend to enable a high resolution and low limit of detection (e.g., down to parts per billion levels) and therefore may be suitable for operations in which low quantities of hydrogen are expected.

Still other embodiments may make use of Raman spectroscopy as another optical method for evaluating hydrogen content of the gas sample. Raman spectroscopy may be advantageous for the complex gas mixtures commonly encountered in drilling fluid logging operations. However, Raman spectroscopy may not have sufficient sensitivity to trace (low) gas concentrations (e.g., owing to weak Raman scattering signals) and may be limited to operations in which higher hydrogen gas concentrations are expected. In certain example embodiments, it may be possible to enhance measurement sensitivity at low hydrogen concentrations using cavity-enhanced Raman spectroscopy (CERS), for example, via using a cavity or multi-pass cell to enhance the interaction length. In other embodiments, increasing the laser power or the gas pressure may also improve the measurement sensitivity.

Figure 11:
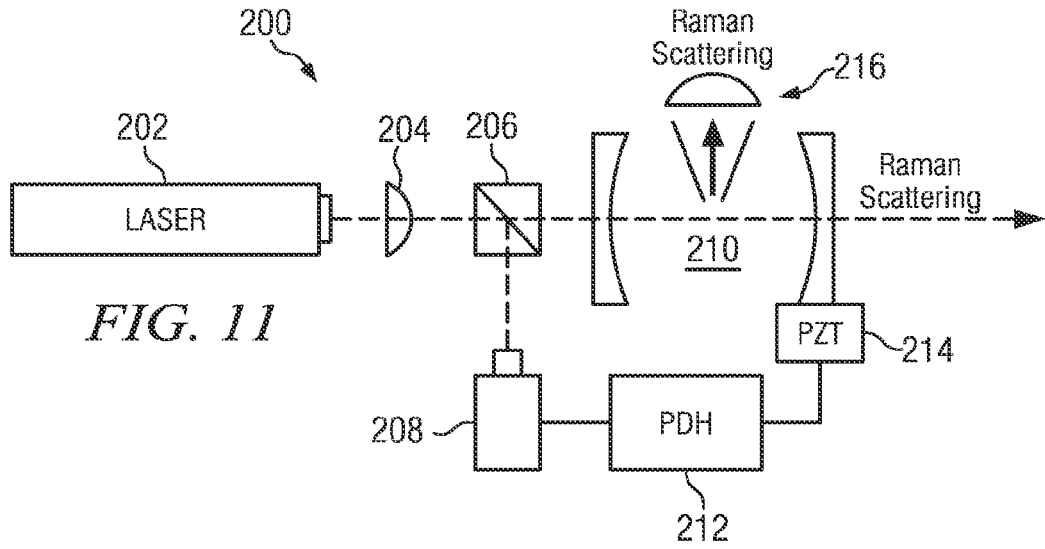
FIG. 11 depicts a schematic diagram of a cavity enhanced Raman spectrometer.

FIG. 11 depicts a schematic diagram of an example cavity-enhanced Raman spectrometer 200 that may be used to evaluate hydrogen gas content in method 100 (FIG. 3). The spectrometer 200 includes a laser source 202 that emits monochromatic light through a mode matching lens 204 and beam splitter 206. Transmitted laser light enters the cavity 210 while reflected light is received at a photodetector 208. The intensity of the received light is input into a Pound-Drever-Hall (PDH) electronic module 212 and provides feedback to modulate the width of the cavity via piezoelectric element 214. Raman scattered photons may then be detected as depicted at 216.

In FIG. 11, the interaction path length (in the cavity) is increased using cavity modulation to enable the detection of small gas concentrations. While not depicted, a notch or dichroic filter may be used to filter out the laser light and enable detection of the Raman signal, especially for small Raman shifts. As mechanical vibrations can offset the cavity length, different precautions may need to be implemented to ensure stable enhancement for those cavities relying on resonant setups. Optical feedback frequency-locking may also be used to modulate the frequency of the laser (e.g., rather than the pathlength of the cavity).

In one example configuration, an intracavity power of about 100 Watts may be achieved using a resonant cavity and 100 mW laser having a wavelength of 532 nm. Such an example system may enable measurement of the most common analytes in the gas stream (e.g., including carbon monoxide, carbon dioxide, and hydrogen gas) with a lower detection limit of about 10 to about 100 ppm and an integration time from about 10 to about 100 seconds. Such a configuration may also enable measurement of the most common hydrocarbons, for example, including lower alkanes and alkenes in the range of 10 ppm to 100 ppm.

Figure 12:
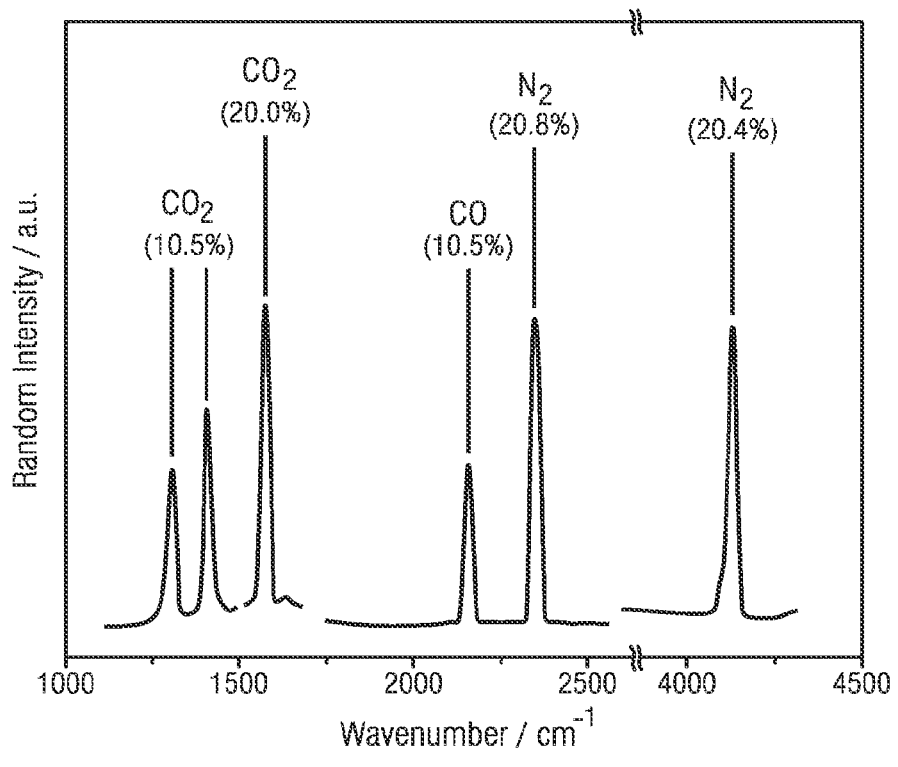
FIG. 12 depicts a plot of Raman spectra of various gases including hydrogen.

FIG. 12 depicts a plot of Raman spectra of various gases including hydrogen (Raman intensity versus wavenumber). The depicted plot includes carbon dioxide, oxygen, carbon monoxide, nitrogen, and hydrogen gases. The quantity of hydrogen and other gases may be determined based on the measured Raman intensity at a specific frequency (wavenumber).

It will be understood that the present disclosure includes numerous embodiments. These embodiments include, but are not limited to, the following embodiments.

In a first embodiment, a method for estimating a quantity of natural hydrogen in a subterranean formation comprises degassing drilling fluid obtained from a wellbore to obtain a gas sample including a quantity of hydrogen gas; measuring a concentration of hydrogen in the gas sample; and applying a correction to the measured concentration of hydrogen to estimate the quantity of natural hydrogen in the subterranean formation.

A second embodiment may include the first embodiment, wherein the degassing comprises drilling the wellbore in the subterranean formation; circulating drilling fluid in the well-bore during the drilling; and degassing the drilling fluid during the circulating to obtain the gas sample.

A third embodiment may include any one of the first through second embodiments, wherein the degassing further comprises sampling gas in a wellbore head space or a return conduit head space, the return conduit head space located between the wellbore and a mud pit; or sampling drilling fluid from the wellbore prior to exposure of the drilling fluid to air and degassing the sampled drilling fluid to obtain the gas sample.

A fourth embodiment may include any one of the first through third embodiments, further comprising: generating a drilling log plotting the estimated quantity of natural hydrogen in the subterranean formation with respect to measured depth in the wellbore.

A fifth embodiment may include any one of the first through fourth embodiments, wherein the applying a correction comprises: measuring a quantity of a second gas in the obtained gas sample; correlating the measured quantity of the second gas with a quantity of drill bit metamorphism (DBM) hydrogen in the obtained gas sample; and subtracting the quantity of DBM hydrogen from the measured hydrogen concentration of the gas sample to compute the estimated quantity of natural hydrogen in the subterranean formation.

A sixth embodiment may include the fifth embodiment, wherein the second gas is selected from the group consisting of carbon monoxide, ethylene, and propylene.

A seventh embodiment may include any one of the first through sixth embodiments, further comprising: calibrating a mass spectrometer for making hydrogen measurements to obtain a calibrated mass spectrometer including a correlation between a measured hydrogen concentration and an actual hydrogen concentration; and wherein the hydrogen concentration of the gas sample is measured using the calibrated gas spectrometer.

An eighth embodiment may include any one of the first through seventh embodiments, wherein: the calibrating the mass spectrometer comprises flushing the mass spectrometer with air and making a background hydrogen concentration measurement; and the method further comprises selecting the mass spectrometer for which the background hydrogen concentration measurement is less than 1000 parts per million.

A ninth embodiment may include the eighth embodiment, wherein calibrating the mass spectrometer further comprises: using the selected mass spectrometer to make hydrogen concentration measurements of corresponding first, second, and third calibration samples, the first, second, and third calibration samples having distinct first, second, and third actual hydrogen concentrations; and evaluating a fit between the first, second, and third actual hydrogen concentrations and the first, second, and third hydrogen concentration measurements to compute the correlation.

A tenth embodiment may include the ninth embodiment, wherein the background hydrogen concentration measurement and the hydrogen concentration measurements of the first, second, and third calibration samples are made via evaluating a mass over charge ratio equal to two.

In an eleventh embodiment, a system for estimating a quantity of natural hydrogen in a subterranean formation comprises: a degasser disposed to degas drilling fluid at a rig site to obtain a gas sample; at least one gas sensor configured to measure a quantity of hydrogen gas and a quantity of a second gas in the gas sample; and a processor configured to evaluate the measured quantity of hydrogen gas and the measured quantity of the second gas to estimate the quantity of natural hydrogen in the subterranean formation.

A twelfth embodiment may include the eleventh embodiment, wherein the at least one gas sensor comprises a calibrated mass spectrometer; and the processor is further configured to apply a correlation to a hydrogen gas concentration measurement made with the calibrated mass spectrometer to obtain the measured quantity of hydrogen gas.

A thirteenth embodiment may include any one of the eleventh through twelfth embodiments, wherein the processor is further configured to evaluate a measured quantity of the second gas to obtain a quantity of drill bit metamorphism (DBM) hydrogen; and subtract the quantity of DBM hydrogen from the measured quantity of hydrogen gas to obtain the estimate of natural hydrogen in the subterranean formation.

A fourteenth embodiment may include any one of the eleventh through thirteenth embodiments, wherein the processor is further configured to generate a drilling log depicting the estimated quantity of natural hydrogen in the subterranean formation and at least one of the measured quantity of hydrogen gas and the measured quantity of the second gas with respect to a depth of a wellbore penetrating the subterranean formation.

A fifteenth embodiment may include any one of the eleventh through fourteenth embodiments, wherein the degasser is disposed to degas drilling fluid from a wellbore penetrating the subterranean formation prior to exposure of the drilling fluid to air.

In a sixteenth embodiment, a method for calibrating a mass spectrometer comprises obtaining a drilling fluid gas sample including a quantity of hydrogen gas; evaluating the drilling fluid gas sample to measure the quantity of hydrogen gas and to measure a quantity of a second gas in the obtained drilling fluid gas sample; correlating the measured quantity of the second gas with a quantity of drill bit metamorphism (DBM) hydrogen in the obtained drilling fluid gas sample; and subtracting the quantity of DBM hydrogen from the measured quantity of hydrogen gas to compute the estimated quantity of natural hydrogen in the subterranean formation.

A seventeenth embodiment may include the sixteenth embodiment, wherein the second gas comprises at least one of carbon monoxide, ethylene, and propylene.

An eighteenth embodiment may include any one of the sixteenth through seventeenth embodiments, wherein the evaluating the drilling fluid gas sample comprises using a calibrated mass spectrometer to measure the quantity of hydrogen gas and the quantity of the second gas in the obtained drilling fluid gas sample.

A nineteenth embodiment may include the eighteenth embodiment, wherein the using the calibrated mass spectrometer to measure the quantity of hydrogen gas comprises using the calibrated mass spectrometer to measure a concentration of hydrogen gas in the gas obtained drilling fluid gas sample; and computing the quantity of hydrogen gas from the measured concentration of hydrogen gas and a calibration correlation for the calibrated mass spectrometer.

A twentieth embodiment may include any one of the eighteenth through nineteenth embodiments, wherein the calibrated mass spectrometer has a background hydrogen concentration measurement that is less than a 1000 parts per million.

Although mud logging of natural hydrogen has been described in detail, it should be understood that various changes, substitutions and alternations can be made herein without departing from the spirit and scope of the disclosure as defined by the appended claims.

What is claimed is:

1. A method for estimating a natural quantity of natural hydrogen in a subterranean formation, the method comprising:

calibrating a mass spectrometer for making hydrogen measurements to obtain a calibrated mass spectrometer including a correlation between a measured hydrogen concentration and an actual hydrogen concentration;

degassing drilling fluid obtained from a wellbore to obtain a gas sample including a sample quantity of hydrogen gas;

measuring a sample concentration of sample hydrogen in the gas sample with the calibrated mass spectrometer; and applying a correction to the sample concentration of the sample hydrogen to estimate the natural quantity of the natural hydrogen in the subterranean formation.

2. The method of claim 1, wherein the degassing comprises:

drilling the wellbore in the subterranean formation;

circulating the drilling fluid in the wellbore during the drilling; and degassing the drilling fluid during the circulating to obtain the gas sample.

3. The method of claim 1, wherein the degassing further comprises:

sampling gas in a wellbore head space or a return conduit head space, the return conduit head space located between the wellbore and a mud pit; or sampling the drilling fluid from the wellbore prior to exposure of the drilling fluid to air and degassing the sampled drilling fluid to obtain the gas sample.

4. The method of claim 1, further comprising:

generating a drilling log plotting the natural quantity of the natural hydrogen in the subterranean formation with respect to measured depth in the wellbore.

5. The method of claim 1, wherein the applying the correction comprises:

measuring a second gas quantity of a second gas in the obtained gas sample;

correlating the second gas quantity of the second gas with a quantity of drill bit metamorphism (DBM) hydrogen in the obtained gas sample; and subtracting the quantity of DBM hydrogen from the sample concentration of hydrogen to compute the natural quantity of the natural hydrogen in the subterranean formation.

6. The method of claim 5, wherein the second gas is selected from the group consisting of carbon monoxide, ethylene, and propylene.

7. The method of claim 1, wherein:

the calibrating the mass spectrometer comprises flushing the mass spectrometer with air and making a background hydrogen concentration measurement; and the method further comprises selecting the mass spectrometer for which the background hydrogen concentration measurement is less than 1000 parts per million.

8. The method of claim 7, wherein calibrating the mass spectrometer further comprises:

using the selected mass spectrometer to make hydrogen concentration measurements of corresponding first, second, and third calibration samples, the first, second, and third calibration samples having distinct first, second, and third actual hydrogen concentrations; and evaluating a fit between the first, second, and third actual hydrogen concentrations and the first, second, and third hydrogen concentration measurements to compute the correlation.

9. The method of claim 8, wherein the background hydrogen concentration measurement and the hydrogen concentration measurements of the first, second, and third calibration samples are made via evaluating a mass over charge ratio equal to two.

10. The method of claim 1, wherein calibrating the mass spectrometer includes calibrating the mass spectrometer using multi-point techniques using at least three gas mixtures having three distinct hydrogen gas concentrations.

11. The method of claim 1, wherein the correlation correlates a hydrogen bias that decreases with increasing hydrogen concentration.

12. The method of claim 11, wherein the hydrogen bias is associated with a background noise level.

13. A system for estimating a natural quantity of natural hydrogen in a subterranean formation, the system comprising:

a degasser disposed to degas drilling fluid at a rig site to obtain a gas sample;

a calibrated mass spectrometer configured to measure a sample concentration of hydrogen gas and a sample quantity of a second gas in the gas sample, wherein the calibrated mass spectrometer is calibrated for making calibrated hydrogen measurements based on a correlation between a measured hydrogen concentration and an actual hydrogen concentration; and a processor configured to evaluate the sample concentration of hydrogen gas and the sample quantity of the second gas and apply a correction to the measured concentration of hydrogen to estimate the natural quantity of the natural hydrogen in the subterranean formation.

14. The system of claim 13, wherein the processor is further configured to:

evaluate a measured quantity of the second gas to obtain a quantity of drill bit metamorphism (DBM) hydrogen; and subtract the quantity of DBM hydrogen from the sample concentration of hydrogen gas to obtain the natural quantity of the natural hydrogen in the subterranean formation.

15. The system of claim 13, wherein the processor is further configured to generate a drilling log depicting the natural quantity of the natural hydrogen in the subterranean formation and at least one of the sample concentration of hydrogen gas and the sample quantity of the second gas with respect to a depth of a wellbore penetrating the subterranean formation.

16. The system of claim 13, wherein the degasser is disposed to degas the drilling fluid from a wellbore penetrating the subterranean formation prior to exposure of the drilling fluid to air.

17. A method comprising:

calibrating a mass spectrometer for making hydrogen measurements to obtain a calibrated mass spectrometer including a correlation between a measured hydrogen concentration and an actual hydrogen concentration;

obtaining a drilling fluid gas sample from a subterranean formation, the drilling fluid gas sample including a quantity of hydrogen gas;

evaluating the drilling fluid gas sample to measure, using the calibrated mass spectrometer, a sample concentration of hydrogen gas and to measure a sample quantity of a second gas in the drilling fluid gas sample;

correlating the sample quantity of the second gas with a quantity of drill bit metamorphism (DBM) hydrogen in the drilling fluid gas sample; and applying a correction to the sample concentration of the hydrogen gas by subtracting the quantity of DBM hydrogen from the sample concentration of hydrogen gas to compute a natural quantity of natural hydrogen in the subterranean formation.

18. The method of claim 17, wherein the second gas comprises at least one of carbon monoxide, ethylene, and propylene.

19. The method of claim 17, wherein the calibrated mass spectrometer has a background hydrogen concentration measurement that is less than a 1000 parts per million.

* * * * *